USOO6468443B1

United States Patent
Wu

(10) Patent No.: US 6,468,443 B1
(45) Date of Patent: Oct. 22, 2002

(54) COLORLESS AND LOW VISCOSITY COMPOUNDS FOR LOW VOLTAGE LIQUID CRYSTAL OPERATION

(75) Inventor: Shin-Tson Wu, Northridge, CA (US)

(73) Assignee: Raytheon Company, Lexington, MA (US)

( * ) Notice: Subject to any disclaimer, the term of this patent is extended or adjusted under 35 U.S.C. 154(b) by 124 days.

(21) Appl. No.: 09/621,588

(22) Filed: Jul. 21, 2000

(51) Int. Cl.[7] .......................... C09K 19/58; C09K 19/54
(52) U.S. Cl. .................... 252/299.5; 252/299.2
(58) Field of Search ................. 252/299.01, 299.4, 252/299.2, 299.66, 299.5

(56) References Cited

U.S. PATENT DOCUMENTS

| 5,338,481 A | 8/1994 | Wu et al. |
|---|---|---|
| 5,370,819 A | 12/1994 | Fujita et al. |
| 5,370,822 A | 12/1994 | Matsui et al. |
| 5,728,319 A | 3/1998 | Matsui et al. |

OTHER PUBLICATIONS

CAPLUS 1988: 630397.*
CAPLUS 1995: 387240.*
CAPLUS 1997: 72252.*
CAPLUS 1999: 601885.*
S–T. Wu et al, "High Solubility and Low Viscosity Dyes for Guest–Hose Displays," Asia Display '95.
Shin–Tson Wu et al, "Liquid Crystal Dyes With High Solubility and Large Dielectric Anisotropy," Applied Physics Letters, vol. 64, No. 17, pp. 2191–2193 (Apr. 25, 1994).
Shin–Tson Wu et al, "Room–Temperature Diphenyl–Diacetylene Liquid Crystals," Applied Physics Letters, vol. 61, No. 6, pp. 630–632 (Aug. 10, 1992).
G. W. Gray, "New Family of Nematic Liquid Crystals for Displays," Electronics Letters, vol. 9, No. 6, pp. 130–131 (Mar. 22, 1973).
A. I. Pavluchenko et al, "Synthesis and Properties of Liquid Crystals With Fluorinated Terminal Substituents," Molecular Crystals and Liquid Crystals, vol. 209, pp. 225–235 (1991).
S. T. Wu et al, "Polarized UV Spectroscopy of Conjugated Liquid Crystals," Journal of Applied Physics, vol. 68, No. 1, pp. 78–85 (Jul. 1, 1990).

S. T. Wu et al, "High Birefringence and Wide Nematic Range Bis–tolane Liquid Crystals," Applied Physics Letters, vol. 74, No. 3, pp. 344–346 (Jan. 18, 1999).
S. T. Wu et al, "Physical Properties of Polar Bis–tolane Liquid Crystals," Japanese Journal of Applied Physics, vol. 39, pp. L38–41 (2000).
S. T. Wu et al, "High Dielectric Dopants for Low Voltage Liquid Crystal Operation," Japanese Journal of Applied Physics, vol. 37, pp. L1254–1256 (1998).

* cited by examiner

Primary Examiner—Shean C. Wu
(74) Attorney, Agent, or Firm—Leonard A. Alkov; Glenn H. Lenzen, Jr.

(57) ABSTRACT

A colorless dopant is provided that has a viscosities approximately the same as that of liquid crystal compositions and supports low voltage operation. The dopants have one of three structures: (1) biphenyl; (2) diphenyl-diacetylene; and (3) double tolane, and in each case, have an amino group (secondary or tertiary) attached at one end of the molecule, with at least one polar group at the other end of the molecule. Schematically, the generic structure may be illustrated as:

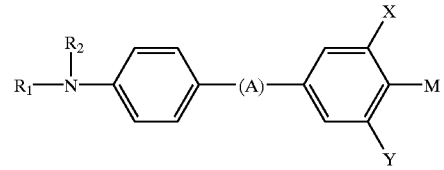

where $R_1$ is an alkyl having from 1 to 12 carbon atoms, $R_2$ is hydrogen or, independently of $R_1$, an alkyl having from 1 to 12 carbon atoms, M is a polar group, X and Y are independently hydrogen or a polar group not necessarily the same as M, and (A) is (1) a single bond (biphenyl); (2) —C≡C—C≡C— (diphenyl-diacetylene); or (3)

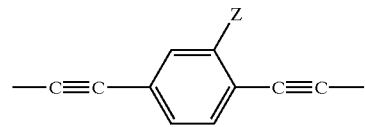

(double tolane), where Z is hydrogen, F, or alkyl.

7 Claims, 1 Drawing Sheet

COLORLESS AND LOW VISCOSITY COMPOUNDS FOR LOW VOLTAGE LIQUID CRYSTAL OPERATION

TECHNICAL FIELD

The present invention is directed generally to liquid crystals, and, more particularly, to improved low voltage operation of liquid crystal devices.

BACKGROUND ART

Liquid crystal display elements utilize the optical anisotropy and the dielectric anisotropy of liquid crystal materials. Various display modes and various driving methods for driving the display modes are well-known.

The properties of liquid crystal materials used for these liquid crystal display devices are various, but any liquid crystal materials have in common stability to moisture, air, heat, light, etc. Further, it is required for the devices that the liquid crystal phases have a temperature range as broad as possible, around room temperature, have a low viscosity, and, in the display device, have a quick response rate, a high contrast, and a comparatively low driving voltage. In addition, it is necessary that the liquid crystal materials have an adequate dielectric anisotropy ($\Delta\epsilon$). However, a single liquid crystal compound satisfying these characteristics apparently has not yet been found. Thus, it is common to blend several different liquid crystal compounds and non-liquid crystal compounds to form a mixture that adequately meets the needs of the specific application.

A few high dielectric anisotropy dye compounds have been reported in literature. Examples include:

1. nitro-amino azobenzenes (I) and nitro-amino-tolanes (II) with structures shown below:

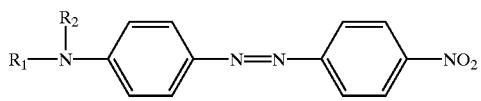

(I)

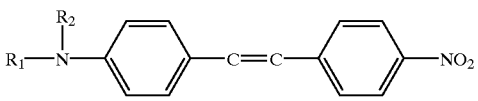

(II)

published by S. T. Wu et al, Asia Display, pp. 567–70 (1995); and 2. bicyano-amino polyene dyes (III) with structures shown below:

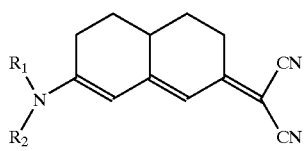

(III)

published by S. T. Wu et al, Japanese Journal of Applied Physics, vol. 37, pp. L1254–1256 (1998).

A general problem with these dyes is that their absorption is too large in the visible region, which causes these dyes to be colored. As a result, light transmission is greatly reduced. This is particularly undesirable for some displays and electro-optic modulators where high transmittance is required. Further, some of these dyes do not provide low voltage operation of the liquid crystal mixture.

Thus, there is a need for dyes that are colorless, have viscosities suitable for liquid crystal applications, approximately 20 mm$^2$/s, and support low voltage operation, with a threshold voltage $V_{th}$ of less than 2 $V_{rms}$.

DISCLOSURE OF INVENTION

In accordance with the present invention, a dopant is provided that is colorless, has a viscosity approximately the same as that of liquid crystal compositions, and supports low voltage operation. The dopants have one of three structures: (1) biphenyl; (2) diphenyl-diacetylene; and (3) double tolane, and in each case, have an amino group (secondary or tertiary) attached at one end of the molecule, with at least one polar group at the other end of the molecule. Schematically, the generic structure may be illustrated as:

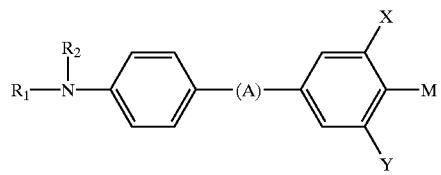

where R$_1$ is an alkyl having from 1 to 12 carbon atoms, R$_2$ is either hydrogen or, independently of R$_1$, an alkyl having from 1 to 12 carbon atoms, M is a polar group, X and Y are independently hydrogen or a polar group not necessarily the same as M, and (A) is (1) a single bond (biphenyl); (2) —C≡C—C≡C— (diphenyl-diacetylene); or (3)

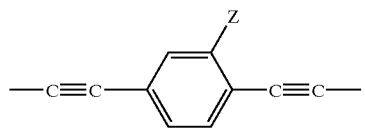

(double tolane), where Z is hydrogen, F, or alkyl.

Also in accordance with the present invention, one or more of the foregoing colorless dopants is added to a liquid crystal composition for supporting low voltage operation.

The teachings of the present invention provide new molecular structures of colorless dopant compounds for low voltage liquid crystal operation. These compounds exhibit an extraordinarily large dielectric anisotropy and relatively low viscosity. Therefore, adding a few percent of such dopant to a liquid crystal mixture reduces the operating voltage significantly while retaining fast response time. The low voltage operation enables use of a low cost electronic driver.

BEST MODES FOR CARRYING OUT THE INVENTION

Figure 1:
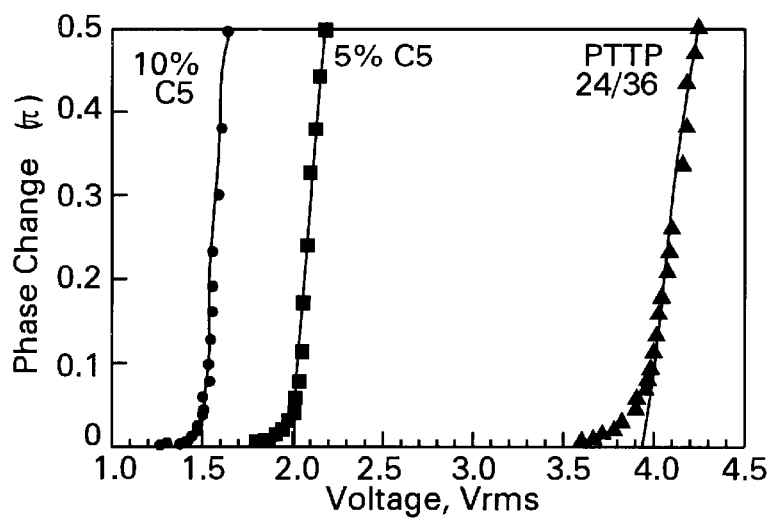
FIG. 1, on coordinates of phase change ($\pi$) and voltage ($V_{rms}$), is a plot depicting the concentration effect of a nitro-amino-tolane compound on the threshold voltage of a liquid crystal mixture designated PTTP-24/36.

Reference is now made in detail to a specific embodiment of the present invention, which illustrates the best mode presently contemplated by the inventor for practicing the invention. Alternative embodiments are also briefly described as applicable.

Low voltage operation of a liquid crystal (LC) device is highly desirable because it enables a low cost electronic driver to be used. Low threshold LC mixtures will find useful application in optical phased arrays for agile beam steering and flat panel display devices.

In the agile beam steering employing a liquid crystal phase modulator, a homogeneous alignment is a preferred approach. Based on the Freedericksz transition, the threshold voltage, $V_{th}$, of a homogeneously aligned liquid crystal cell is governed by the splay elastic constant ($K_{11}$) and dielectric anisotropy ($\Delta \epsilon$) of the liquid crystal material as $V_{th} = \pi (K_{11}/\Delta \epsilon)^{1/2}$. A simple way to reduce $V_{th}$ is to use liquid crystals having high $\Delta \epsilon$ values, that is, polar liquid crystals with a large dipole moment, such as a cyano group. The shortcoming of this approach are twofold: (1) these polar liquid crystals normally possess a high melting temperature and narrow nematic range, and (2) the dielectric anisotropy of these polar liquid crystals is usually lower than 20.

The push-pull effect has been investigated in some dye molecules, e.g., the nitro-amino-azo dyes (I) and nitro-amino-tolane dyes (II) as shown below; see, S. T. Wu et al, Applied Physics Letters, vol. 64, pp. 2191–2193 (1994) and the Asia Display reference, supra:

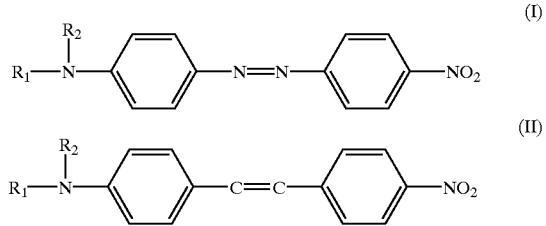

where $R_1$ is an alkyl group or an alkoxy group having from 1 to 12 carbon atoms ($C_nH_{2n+1}$ or $OC_nH_{2n+1}$) where n=1–12) or an alkenyl group or an alkenyloxy group having from 2 to 12 carbon atoms ($C_nH_{n-1}$ or $OC_nH_{2n-1}$) and $R_2$ is H or, independently of $R_1$ is an alkyl group or an alkoxy group having from 1 to 12 carbon atoms or an alkenyl group or an alkenyloxy group having from 2 to 12 carbon atoms.

The dielectric anisotropy of these compounds (I) and (II) is around 60. Thus, adding a few percent of such compound to a binary nonpolar diphenyl-diacetylene liquid crystal mixture PTTP-24/36 would reduce the threshold voltage noticeably. This mixture is disclosed by S. T. Wu et al, Applied Physics Letters, vol. 61, pp. 630–632 (1992) and in U.S. Pat. No. 5,338,451, issued Aug. 16, 1994. The addition of (II) to PTTP-24/36 is disclosed and claimed in related application Ser. No. 09/614,443, filed Jul. 12, 2000 [PD-99E115].

Diphenyl-diacetylene liquid crystals are known to exhibit a high birefringence, low viscosity, wide nematic range, and small heat fusion enthalpy. They have been used extensively in optical phased arrays. The structure of a diphenyl-diacetylene liquid crystal is shown below.

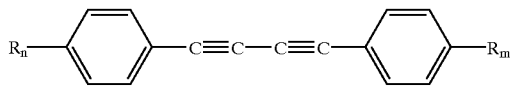

where $R_n$ and $R_m$ are alkyl groups, independently having from 1 to 12 carbon atoms.

These compounds are abbreviated as PTTP-nm, where "PTTP" is an abbreviation for phenyl-triple bond-triple bond-phenyl. A binary mixture has been formulated using PTTP-24 and PTTP-36 at 1:1 ratio, designated PTTP-24/36, mentioned above.

FIG. 1 depicts the effect of doping the PTTP-24/36 eutectic mixture with 5 and 10% of compound (II) with $R_1 = C_5H_{11}$ and $R_2 = H$. The threshold voltage is reduced from 3.85 to 2.0 and 1.5 $V_{rms}$ for the 5% and 10% concentration, respectively. The visco-elastic coefficient ($\gamma_1/K_{11}$) of these two guest-host mixtures were measured to be ~19 ms/$\mu$m$^2$, which is nearly the same as the host PTTP-24/36 binary mixture.

Thus, doping such dye will lower the operating voltage while keeping response time unaffected.

Figure 2:
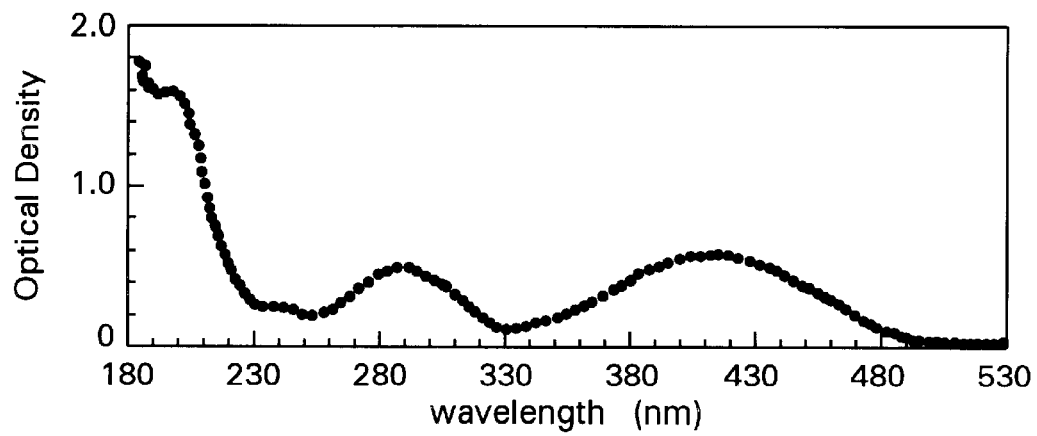
FIG. 2, on coordinates of optical density and wavelength (nm), depicts the optical density of a 6 μm homogeneous cell containing 1% nitro-amino tolane dye dissolved in a liquid crystal mixture designated ZLI-2359.

However, compounds (I) and (II) are dyes; their colors are red and orange, respectively. Their absorption tail extends to the visible spectral region as shown in FIG. 2 for the 1% tolane dye in a ZLI-2359 liquid crystal host mixture. ZLI-2359 is a mixture of bicyclohexanes available from Merck & Co. This UV-transparent host mixture was used for the absorption measurement of the tolane. The cell gap used for this measurement was ~6 $\mu$m. The peak absorption of the nitro-amino-tolane is centered at about 420 nm and extends to nearly 500 nm. While these compounds may find use in particular applications, it is desired in other applications to use colorless compounds.

To eliminate absorption in the visible region while maintaining the desirable large dielectric anisotropy and low viscosity, three series of strong polar, but colorless compounds, have been devised: (1) biphenyls; (2) diphenyl-diacetylenes, and (3) double tolanes. Schematically, the generic structure may be illustrated as:

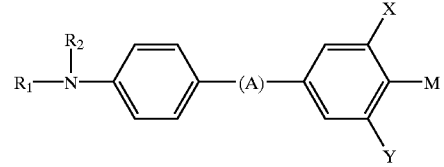

where $R_1$ is an alkyl having from 1 to 12 carbon atoms, $R_2$ is either hydrogen or, independently of $R_1$, an alkyl having from 1 to 12 carbon atoms, M is a polar group, X and Y are independently hydrogen or a polar group not necessarily the same as M, and (A) is (1) a single bond (biphenyl); (2) —C≡C—C≡C— (diphenyl-diacetylene); or (3)

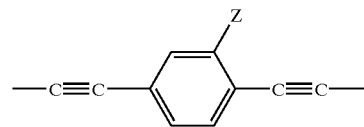

(double tolane), where Z is hydrogen, F, or alkyl. Each class of compounds is discussed separately below.

1. Biphenyls

Biphenyl liquid crystals, such as disclosed by G. W. Gray et al, Electronics Letters, vol. 9, pp. 130–131 (1973), have been used extensively for flat panel displays, such as wrist watches. Here, the biphenyl core is combined with the push-pull agents. Two types of electron donor (CN and CF$_3$) are listed below as examples. Other polar group, such as OCF$_3$, CHF$_2$ etc., can be considered as well; see, e.g., A. I. Pavluchenko et al, Molecular Crystals and Liquid Crystals, vol. 209, pp. 225–235 (1991). Alternatively, yet another polar group, F, may be employed.

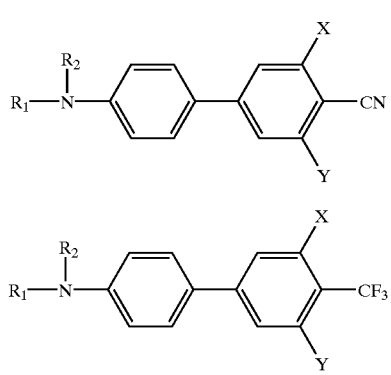

(1.1)

(1.2)

where $R_1$ and $R_2$ are as defined above.

Both CN and $CF_3$ are strong polar groups. The dipole moment of CN is somewhat stronger than that of $CF_3$. However, the $CF_3$ group possesses a lower viscosity, higher resistivity, and shorter absorption wavelength, and is more favorable than the CN group from a colorless viewpoint. High resistivity is required for the thin-film-transistor (TFT) based liquid crystal displays. The side chain $R_1$ and $R_2$ make important contributions to the melting temperature and viscosity of these compounds. A longer side chain would normally lead to a lower melting temperature and higher viscosity. To further enhance dielectric anisotropy, another polar group, such as F or Cl, can be substituted in the X and/or Y positions (3 and/or 5 positions). This lateral substitution not only lowers the melting temperature but increases $\Delta\epsilon$. Due to c hindrance considerations, the polar group in the X and/or Y positions is smaller the group in the para, or 4, position.

Examples of biphenyl compounds have been prepared and their melting points (m.p.) and heats of enthalpy ($\Delta$H) determined. The results are listed in the Table below for the various compounds.

TABLE

Biphenyl dopants and their properties.

| Cmpd | $R_1$ | $R_2$ | M | X | Y | m.p., °C. | $\Delta$H, Kcal/mol |
|---|---|---|---|---|---|---|---|
| 1 | —$CH_3$ | —$CH_3$ | CN | H | H | 219.5 | 7.10 |
| 2 | —$C_2H_5$ | —$C_2H_5$ | CN | H | H | 159* | 7.28 |
| 3 | —$CH_3$ | —$CH_3$ | F | H | H | 169 | 7.28 |
| 4 | —$C_2H_5$ | —$C_2H_5$ | F | F | F | 86.6* | 6.8 |

Note:
*The extrapolated $\Delta\epsilon$ value (from 10% concentration in PTTP-24/36 host) for Compounds #2 and #4 is 26 and 25, respectively.

Figure 3:
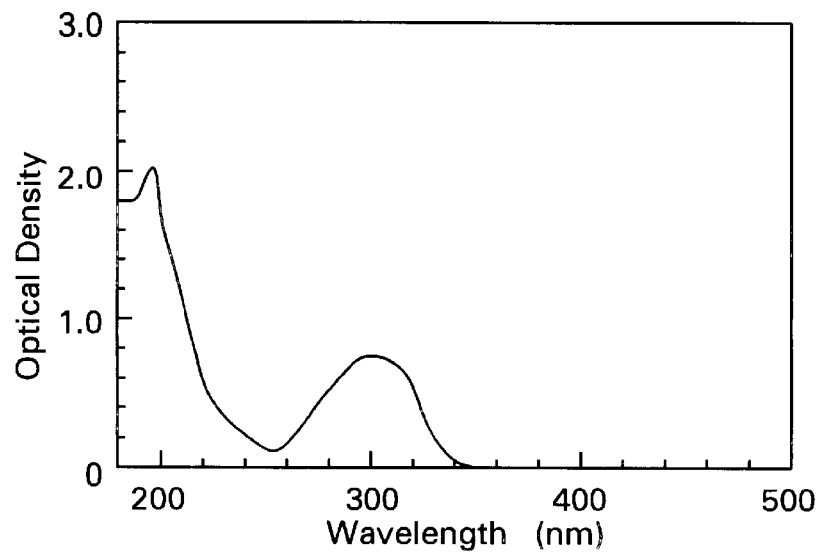
FIG. 3, on coordinates of optical density and wavelength (in nm), is a plot of an absorption curve of 4-dimethyl amino-4'-fluoro biphenyl, showing that it is a colorless compound.

FIG. 3 shows the absorption spectrum of 1 wt % of the third biphenyl compound in the above Table ($R_1=R_2=CH_3$; M=F; X=Y=H) in the liquid crystal mixture designated ZLI-2359, using a 6 μm cell. The compound is seen to be colorless in the visible spectrum.

2. Diphenyl-Diacetylenes

In the alkyl-alkyl diphenyl-diacetylene structure, the absorption extends to ~340 nm; see, e.g., S. T. Wu et al, Journal of Applied Physics, vol. 68, pp. 78–85 (1990). Adding an amino group would extend the absorption to ~400 nm. Thus, the cyano group, which is a strong electron acceptor, cannot be used. Under this circumstance, the $CF_3$ is a better choice in order to maintain colorless.

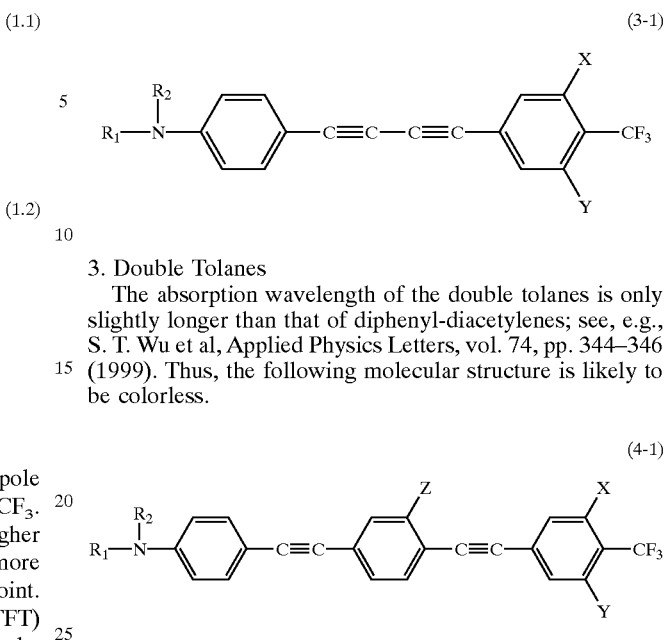

(3-1)

3. Double Tolanes

The absorption wavelength of the double tolanes is only slightly longer than that of diphenyl-diacetylenes; see, e.g., S. T. Wu et al, Applied Physics Letters, vol. 74, pp. 344–346 (1999). Thus, the following molecular structure is likely to be colorless.

(4-1)

To lower the melting temperature of such a highly conjugated molecule and improve its solubility, the side chain ($R_1$ and $R_2$) length may be varied, or the hydrogen(s) in the lateral position(s) (X and/or Y) may be replaced by a polar (e.g., F or Cl) group, as with the diphenyl-diacetylenes above. Further, the substitution of Z with a polar group (F or Cl) or an alkyl ($C_nH_{2n+1}$) group may be used to lower the melting temperature substantially, see, e.g., S .T. Wu, Japanese Journal of Applied Physics, vol. 39, pp. L38–41 (2000). These lateral groups serve to increase the molecular breadth and weakening the intermolecular associations. As a result, the melting temperature is lowered significantly.

4. Further Considerations

The amount of the colorless dopant added to the liquid crystal composition, which comprises at least one liquid crystal compound, is in an effective amount to achieve the elimination of absorption of light by the liquid crystal composition in the visible region while maintaining a desirable large dielectric anisotropy and low viscosity. Preferably, the amount of the dopant added is within the range of about 1 to 20 wt % of the total liquid crystal composition, and more preferably, about 5 to 10 wt %.

The purposes of the addition of the colorless dopants of the present invention include:

(1) reduction of the operation voltage of liquid crystal devices;

(2) maintenance of high transmittance in the visible region; and (3) retention of fast response time.

The advantages provided by the colorless dopants of the present invention include:

(1) these compounds are colorless (their electronic absorptions appear in the ultraviolet region);

(2) they possess a very large dielectric anisotropy;

(3) their viscosity is relatively low; and (4) they help reduce operation voltage for both polar and nonpolar LC mixtures.

INDUSTRIAL APPLICABILITY

The colorless dopants of the present invention are expected to find use in the reduction of operating voltages of liquid crystal devices while retaining fast response time.

What is claimed is:

1. A colorless dopant for addition to liquid crystal compositions for reduction of operating voltage of devices employing such liquid crystal compositions, said dopant having a structure selected from the group consisting of (a)

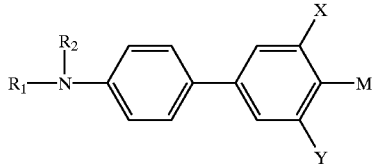

where $R_1=R_2=C_2H_5$, $M=X=Y=F$, and (b)

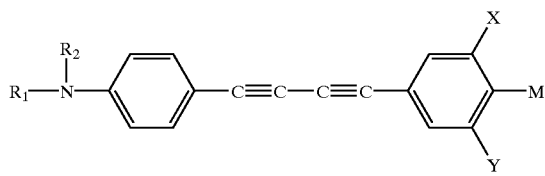

where $R_1$ is an alkyl having from 1 to 12 carbon atoms, $R_2$ is either hydrogen or, independently of $R_1$, an alkyl having from 1 to 12 carbon atoms, M is a polar group, and X and Y are independently hydrogen or a polar group not necessarily the same as M.

2. The dopant of claim 1 wherein said polar group is selected from the group consisting of CN, $CF_3$, $OCF_3CHF_2$, F, and Cl.

3. A method for reducing operating voltage of a liquid crystal composition comprising at least one liquid crystal compound, said method comprising adding to said liquid crystal composition an effective amount of a dopant selected from the group consisting of (1) a biphenyl given by the formula

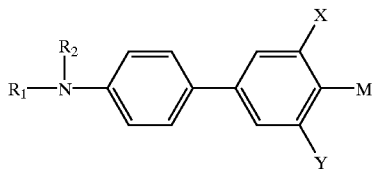

where $R_1=R_2=C_2H_5$, $M=X=Y=F$;

(2) diphenyl-diacetylenes given by the formula

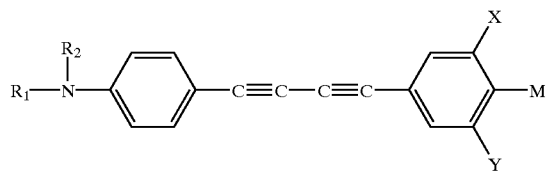

where $R_1$ is an alkyl having from 1 to 12 carbon atoms, $R_2$ is either hydrogen or, independently of $R_1$, an alkyl having from 1 to 12 carbon atoms, M is a polar group, and X and Y are independently hydrogen or a polar group not necessarily the same as M; and (3) double tolanes given by the formula

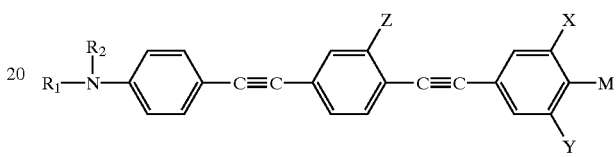

where $R_1$ is an alkyl having from 1 to 12 carbon atoms, $R_2$ is either hydrogen or, independently of $R_1$, an allyl having from 1 to 12 carbon atoms, M is a polar group, X and Y are independently hydrogen or a polar group not necessarily the same as M, and Z is hydrogen, F, or alkyl.

4. The method of claim 3 wherein said polar group is selected from the group consisting of CN, $CF_3$, $OCF_3$, $CHF_2$, F, and Cl.

5. The method of claim 3 wherein said effective amount is within the range of 1 to 20 wt % of said liquid crystal composition.

6. The method of claim 5 wherein said effective amount is within the range of 5 to 10 wt %.

7. The method of claim 3 wherein said at least one liquid crystal compound has the formula

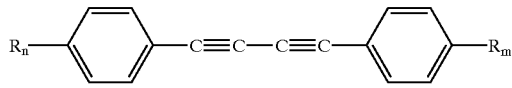

where $R_n$ and $R_m$ are alkyl groups, independently having from 1 to 12 carbon atoms.

* * * * *